United States Patent [19]
Sato et al.

[11] Patent Number: 5,733,877
[45] Date of Patent: Mar. 31, 1998

[54] PHARMACEUTICAL COMPOSITION CONTAINING BIOLOGICALLY ACTIVE PEPTIDE OR PROTEIN

[75] Inventors: Makoto Sato; Toshiyuki Kouzaki; Yoko Ishihara; Shigeaki Yoshina; Masanao Nakoshi; Tatsushi Maeda, all of Aichi-ken, Japan

[73] Assignee: Sanwa Kagaku Kenkyusho Co., Ltd., Nagoya, Japan

[21] Appl. No.: 503,479

[22] Filed: Jul. 18, 1995

[30] Foreign Application Priority Data

Jul. 22, 1994 [JP] Japan .................... 6-171070

[51] Int. Cl.$^6$ .................... A61K 9/107; A61K 38/02; A61K 38/22; A61K 38/23
[52] U.S. Cl. .................... 514/12; 514/2; 514/13; 514/21; 514/938
[58] Field of Search .................... 514/2, 12, 13, 514/21, 938

[56] References Cited

U.S. PATENT DOCUMENTS

| | | | |
|---|---|---|---|
| 4,507,279 | 3/1985 | Okuyama et al. | 514/772 |
| 4,877,606 | 10/1989 | Churchill et al. | 424/486 |
| 5,214,030 | 5/1993 | Stief | 514/12 |
| 5,310,727 | 5/1994 | Lattanzi et al. | 514/12 |
| 5,444,041 | 8/1995 | Owen et al. | 514/2 |
| 5,472,706 | 12/1995 | Friedman et al. | 424/450 |
| 5,496,818 | 3/1996 | Schaupp et al. | 514/225.8 |
| 5,514,670 | 5/1996 | Friedman et al. | 514/2 |
| 5,576,016 | 11/1996 | Amselem et al. | 424/450 |

FOREIGN PATENT DOCUMENTS

| | | |
|---|---|---|
| 56-167616A | 12/1981 | Japan . |
| 56-216820A | 12/1984 | Japan . |
| 61-263914A | 11/1986 | Japan . |
| 62-284000A | 12/1987 | Japan . |

OTHER PUBLICATIONS

Muranishi S. "Proceed. Intern. Symp. Control. Rel. Bioact. Mater.", vol. 19, pp. 212–213 (1992).

*Primary Examiner*—Jeffrey E. Russel
*Attorney, Agent, or Firm*—Nikaido Marmelstein Murray & Oram

[57] ABSTRACT

A pharmaceutical composition is disclosed comprising a fat emulsion containing microspheres and having its electric charge adjusted to a negative value and a biologically active substance selected from the group consisting of a basic peptide and a basic protein, which biologically active substance is adsorbed to the microspheres in the fat emulsion. An acidic phospholipid, a fatty acid, a bilic acid and a salt of such substances is preferred as an agent for adjusting the electric charge of the fat emulsion. Motilin derivatives, vasoactive intestinal polypeptide derivatives and calcitonin are preferred biologically active substances.

3 Claims, 8 Drawing Sheets

□ : Fat emulsion (Prescription A, 0.1%) + Motilin analogue
+ : Fat emulsion (Prescription A, 0.2%) + Motilin analogue
◇ : Fat emulsion (Prescription A, 0.5%) + Motilin analogue
△ : Fat emulsion (Prescription A, 1.0%) + Motilin analogue □ : Fat emulsion (Prescription A) + Motilin analogue
   Y = 0.14946 X + 1.96688
   R = 0.98147

◇ : Fat emulsion (Prescription B) + Motilin analogue
   Y = 0.14512 X + 2.18766
   R = 0.98582

☐ : Fat emulsion (Prescription A, 0.1%) + Motilin analogue
+ : Fat emulsion (Prescription A, 0.2%) + Motilin analogue
◇ : Fat emulsion (Prescription A, 0.5%) + Motilin analogue
△ : Fat emulsion (Prescription A, 1.0%) + Motilin analogue □ : Fat emulsion (Prescription B, 0.1%) + Motilin analogue
+ : Fat emulsion (Prescription B, 0.2%) + Motilin analogue
◇ : Fat emulsion (Prescription B, 0.5%) + Motilin analogue
△ : Fat emulsion (Prescription B, 1.0%) + Motilin analogue □ : Aqueous solution of motilin analogue (Control)
+ : Motilin analogue composition containing fat emulsion □ : Aqueous solution of motilin analogue (Control)
+ : Motilin analogue composition containing fat emulsion □ : Aqueous solution of motilin analogue (Control)
+ : Motilin analogue composition containing fat emulsion □ : Aqueous solution of motilin analogue (Control)
+ : Motilin analogue composition containing fat emulsion + : Aqueous solution of VIP analogue (Control)
◇ : VIP analogue composition (Test sample B)
△ : VIP analogue composition (Test sample C)

△ : Aqueous solution of VIP analogue (Control)
○ : VIP analogue composition (Test sample B)
● : VIP analogue composition (Test sample C)
□ : VIP analogue composition (Test sample D)
■ : VIP analogue composition (Test sample E)

☐ : Buffer
+ : Fat emulsion
◇ : Control (amount 0.03µ g/ml/kg)
△ : Control (amount 0.10µ g/ml/kg)
+ : Test Sample (amount 0.03µ g/ml/kg)

PHARMACEUTICAL COMPOSITION CONTAINING BIOLOGICALLY ACTIVE PEPTIDE OR PROTEIN

BACKGROUND OF THE INVENTION

1. Field of the Invention

The present invention relates to a pharmaceutical composition containing a biologically active peptide or protein.

2. Related Arts

In recent years, various trials have been made on a biologically active substance (hereinafter referred to as "drug") to increase its pharmacological activity by making it into a preparation or medicine in the form of a fat emulsion. For instance, such fat emulsions have been proposed, as on a steroid [Jap. Pat. Sho 56 (A.D. 1981)-167616(A)], prostaglandin [Jap. Pat. Sho 59 (A.D. 1984)-216820(A)] and anti-tumor agent [said Jap. Pat. Sho 56 (A.D. 1981)-167616(A)], and an increase in pharmacological activity has been somewhat recognized. However, it is difficult to emulsify a water-soluble drug and thus such methods have been proposed, as that a fat-soluble functional group is introduced into a molecule of lower fat-soluble drug [said Jap. Pat. Sho 56 (A.D. 1981)-167616(A)], and that 1-dodecylhexahydro-2-azepin-2-one (abbreviated as "AZONE") or the like substance having higher solubility of the drug is mixed to oil-phase component for the fat emulsion [Jap. Pat. Sho 61 (A.D. 1986)-263914(A)].

In general, a biologically active peptide or protein is poor in fat-solubility and thus it is impossible to prepare a fat emulsion by the methods as referred to above, and a simple adsorption by mixing provides a low adsorption ratio or efficiency and the adsorptive is apt to coming off. Therefore, such a method has been proposed that the biologically active protein is chemically linked by covalent bond on lipid microspheres in the fat emulsion [Jap. Pat. Sho 62 (A.D. 1987)-284000(A)].

It is necessary to dissolve, adsorb or link a drug to microspheres in the fat emulsion and to control discharge of the drug in vivo, in case of that the fat emulsion is utilized as a drug carrier to give various functions to the drug, such as improvements in properties of the drug (improvement in stability and dispersive power, reduction in stimulation and the like), and to give targeting ability against a desired internal organ or tissue, whereby the drug sufficiently develops its activity.

The dissolution, adsorption or linkage of the drug to the microspheres and the drug discharge control are determined by a drug distribution between oil-phase component (for instance, soybean oil) or interface component (for instance, egg yolk lecithin) and water-phase (for instance, serum in case of in vivo). Hitherto, the drug distribution has been controlled based on a fat-solubility of the drug. Namely, the conventional drug distribution control has been made by (a) selection of oil component for the fat emulsion (to select the component as much as suitable to fat-solubility of the drug), or (b) improvement in fat-solubility of the drug by chemical modification thereof.

Among these methods, the method (a) has disadvantages in that an oil or fat component for maintaining the form as fat emulsion is limited, that kind of the drug is also limited, and that it can not be applied for a peptide or the like hydrophilic drug. According to the method (b), the drug distribution control is possible in some extent, but this method has also disadvantages in that a prodigious labor is required on chemical modification of the drug and on evaluation in change of drug properties (activity, toxicity and the like) due to the modification, and that there is such a possibility that activity of the modified drug decreases or disappears. In the chemical modification of a peptide or protein for increasing fat-solubility thereof, in fact, a remarkable decrease of the drug activity has been reported [Muranishi S., "Proceed. Intern. Symp. Control. Rel. Bioact. Mater.", Vol. 19, pages 212-213 (1992)]. The drug distribution control according to the method (b) can only be applied for limited drugs.

SUMMARY OF THE INVENTION

An object of the invention, therefore, lies in providing a pharmaceutical composition in the form of a fat emulsion, which contains a hydrophilic drug and more particularly, a biologically active peptide or protein without decreasing its activity.

The inventors have energetically studied and investigated to find out that a biologically active basic peptide or protein can be adsorbed or linked on or to microspheres in a fat emulsion with high efficiency by adjusting electric charge of the emulsion to negative, that discharge and distribution of the peptide or protein can be controlled by an amount of the electric charge adjusting agent, that stability of the peptide or protein to enzymes is increased, that pharmacological activity thereof increases, and that duration of pharmacological effect can be extended, whereby the invention has been established.

As the electric charge adjusting agent, at least one of such substances can be selected, as acidic phospholipids, fatty acids, bilic acids, and salts of these compounds. As the acidic phospholipids, phosphatidylserine, phosphatidylglycerol, phosphatidylinositol, phosphatidic acid and the like can be listed. There is no limitation on the fatty acid, but it is preferable to select those having 6 or more carbon atoms. As the bilic acids, dehydrocholic acid, deoxycholic acid, and taurocholic acid and the like can be listed.

There is also no limitation on the biologically active basic peptide and protein, but exemplary compounds are motilin, vasoactive intestinal polypeptide (VIP), glucagon, calcitonin as well as analogues and derivatives of such peptides.

The electric charge adjusting agent containing fat emulsion can be prepared in any manner and with any prescription known per se in the art, excepting addition of the electric charge adjusting agent. For instance, the fat emulsion can be prepared by adding an oil or fat (for instance, a simple lipid) in an amount not higher than 50% (W/V) to total amount, an emulsifier (for instance, a phospholipid) in amount of 0.1-2.4 in weight ratio to the oil or fat, an electric charge adjusting agent in required amount and if necessary, an emulsifying aid, a stabilizer and the like, uniformly mixing the substances by heating or distilling out a solvent that dissolves them, adding water in a suitable amount and if necessary adding pH adjusting agent, isotonic agent and the like, and homogenizing the mixture by a conventional homogenizer. An amount of the electric charge adjusting agent can be properly determined and in case of the phospholipid, it can be added in amount of 100 mol% in maximum to the emulsifier. In case of another electric charge adjusting agent, it may be added 50 mol% in maximum to the total amount of the emulsifier.

An adsorption or linkage of the basic peptide or protein on or to microspheres in the fat emulsion can be attained by mixing the electric charge adjusted fat emulsion with an aqueous solution of the basic peptide or protein, adjusting pH to that lower than isoelectric point of the latter, and leaving the mixture as it is.

DETAILED DESCRIPTION OF PREFERRED EMBODIMENTS

Figure 1:
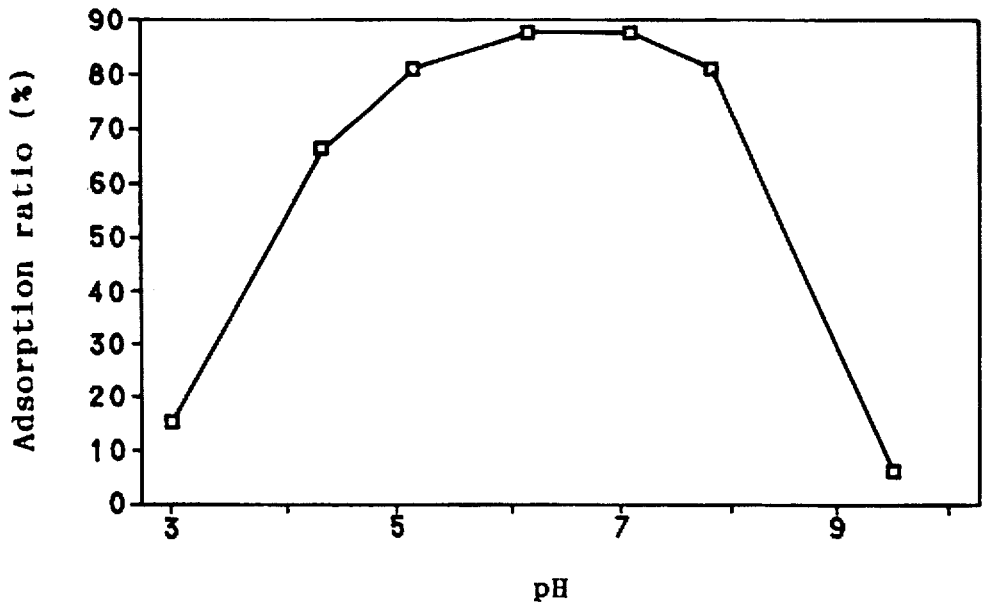
FIG. 1 is a graph showing a relation between pH condition and an adsorption ratio of motilin analogue adsorbed to microspheres in a fat emulsion which was prepared by using squalane as a fat, hydrogenated soybean phosphatidylcholine as an emulsifier and sodium dimyristoylphosphatidylglycerol as an electric charge adjusting agent.

The invention will now be further explained in more detail with reference to Manufacturing Examples and Test Examples.

Example 1 and Test Example 1

An electric charge adjusting agent (0.4g) shown in Table 1 given later, purified egg yolk lecithin (1.6g) and soybean oil (8.0g) were added into a solution of chloroform/methanol (50ml, 5/1, V/V) to mix for dissolving solid components and then the solvents were completely removed in vacuo by a rotary evaporator. To the residue, added distilled water (90g) for injection and treated by a homogenizing mixer (10,000 rpm) to obtain a crude emulsion. The crude emulsion was high-pressure emulsified (1500 kg/cm$^2$) by a microfluidizer to obtain 10% (W/W) fat emulsion.

The fat emulsion was mixed with an aqueous solution of motilin analogue ([Leu$^{13}$]-motilin-homoserine, Amino acid sequence: Phe-Val-Pro-Ile-Phe-Thr-Tyr-Gly-Glu-Leu-Gln-Arg-Leu-Gln-Glu-Lys-Glu-Arg-Asn-Lys-Gly-Gln-Hse [SEQ. ID. NO:1], prepared by the assignee company), pH and ion intensity of the mixture being adjusted to 7 by sodium hydroxide solution and 0.308 by sodium chloride solution, respectively to obtain a desired pharmaceutical composition [Final component concentrations: 1% (W/W) fat emulsion, and 50 μg/ml motilin analogue].

Each of the resulting pharmaceutical compositions was ultrafiltrated by using an ultrafilter (fractional molecular weight: 30,000), motilin analogue adsorption of which was previously saturated by a solution of the motilin analogue to quantitatively measure a concentration of the motilin analogue in a filtrate to calculate an amount of the motilin analogue adsorbed to microspheres in the fat emulsion.

Results are shown in following Table 1. As apparently seen therefrom, adsorption ratio of the motilin analogue in each electric charge adjusting agent added fat emulsion is far greater than that of the control, in which no electric charge adjusting agent was added, and it reached higher than 80%.

TABLE 1

| Electric charge adjusting agent | Adsorption ratio (%) |
| --- | --- |
| Dimyristoylphosphatidylglycerol (Na) | 100 |
| Sodium dimyristoylphosphatate | 100 |
| Phosphatidylinositol (Na) | 100 |
| Phosphatidylserine | 100 |
| Oleic acid | 82.3 |
| Sodium caprate | 93.1 |
| Control | 13.0 |

Example 2 and Test Example 2

Each of electric charge adjusted fat emulsions was prepared as described in Example 1 excepting that an oil or fat shown in Table 2 given later (8.0g), hydrogenated soybean phosphatidylcholine (1.2g) and sodium dimyristoylphosphatidylglycerol (0.8g) as the electric charge adjusting agent were selected. The fat emulsion was mixed with an aqueous solution of the motilin analogue as described in Example 1 to obtain a pharmaceutical composition [Final component concentrations: 0.1% (W/W) fat emulsion, and 100 μg/ml motilin analogue].

An adsorption ratio of the motilin analogue was calculated as in Test Example 1.

Results are shown in following Table 2. As apparently seen therefrom, kind of the oil and fat does not give any influence on adsorption of the motilin analogue to microspheres in the fat emulsion.

TABLE 2

| Oil or fat | adsorption ratio (%) |
| --- | --- |
| Soybean oil | 85.9 |
| Middle-chain length fatty triglyceride | 86.2 |
| Tocopherol acetate | 86.9 |
| Squalane | 87.3 |

Example 3 and Test Example 3

By using the fat (squalane) emulsion prepared by Example 2, a pharmaceutical composition, in which one of following peptides and a derivative thereof is absorbed to microspheres in the fat emulsion, was prepared (ion intensity: 0.308, pH 7, final component concentrations: 0.1% fat emulsion and 100 µg/ml peptide).

(a) [Leu$^{17}$]-VIP-Hse: His-Ser-Asp-Ala-Val-Phe-Thr-Gly-Asn-Tyr-Thr-Lys-Leu-Arg-Lys-Gln-Leu-Ala-Ala-Lys-Lys-Tyr-Leu-Asn-Lys-Ala-Leu-Lys-Hse [SEQ. ID. NO:2]

(b) [Leu$^{17}$]-VIP-Hse-hexylamide (c) Eel calcitonin (d) [Leu$^{13}$]-motilin-Hse Adsorption ratio of each composition was measured as described in Test Example 1 and total quantity of electric charge at pH 7 was calculated based on structural amino acids of the peptide.

Results are shown in following Table 3. As apparently seen therefrom, the peptides (a) and (c) as well as the derivative (b) have higher total electric charge than the motilin analogue (d), so that they are completely adsorbed to microspheres in the fat emulsion.

TABLE 3

| Peptide | Total electric charge | Adsorption ratio (%) |
| --- | --- | --- |
| a | +6.5 | 100 |
| b | +7.5 | 100 |
| c | +2.5 | 100 |
| d | +1 | 87.3 |

Test Example 4

ζ-Potential of the squalane emulsion obtained by Example 2 was measured under conditions of ion intensity of 0.308 and pH 3–9.5. Further, an amount of the motilin analogue adsorbed to microspheres in the pharmaceutical composition obtained by Example 2 (final component concentrations: 0.1 fat emulsion, and 100 µg/ml [Leu$^{13}$]-motilin-Hse) was measured under conditions of ion intensity of 0.308 and pH 3–9.5.

Figure 2:
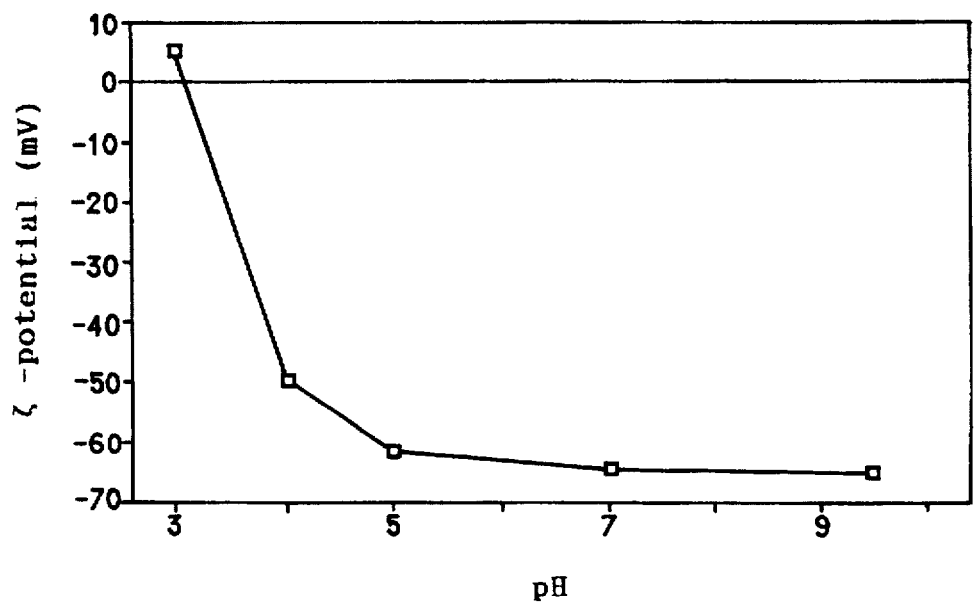
FIG. 2 is a graph showing a relation between pH condition and ζ-potential of the fat emulsion referred to on FIG. 1.

Results are shown in FIGS. 1 and 2. As apparently seen therefrom, the motilin analogue shows good adsorption to microspheres in the fat emulsion in a pH range of less than its isoelectric point (pH 8.6) and in that the fat emulsion has negative charge.

Example 4 and Test Example 5

A fat emulsion was prepared as described in Example 1 by using squalane (8.0 g) as an oil, hydrogenated soybean phosphatidylcholine (1.8 g) as an emulsifier and sodium dimyristoylphosphatidylglycerol (0.2 g) as an electric charge adjusting agent.

The fat emulsion (Prescription A) or the other fat emulsion (Prescription B) as described in Example 2, which is different from the Prescription A in the amount of electric charge adjusting agent was mixed as described in Example 1 with an aqueous solution of [Leu$^{13}$]-motilin-Hse under conditions of ion intensity of 0.308 and pH 7 (final component concentrations: 0.1% fat emulsion, and 50–500 µg/ml motilin analogue) to check an amount of the motilin analogue adsorbed to microspheres in each of the fat emulsions.

Figure 3:
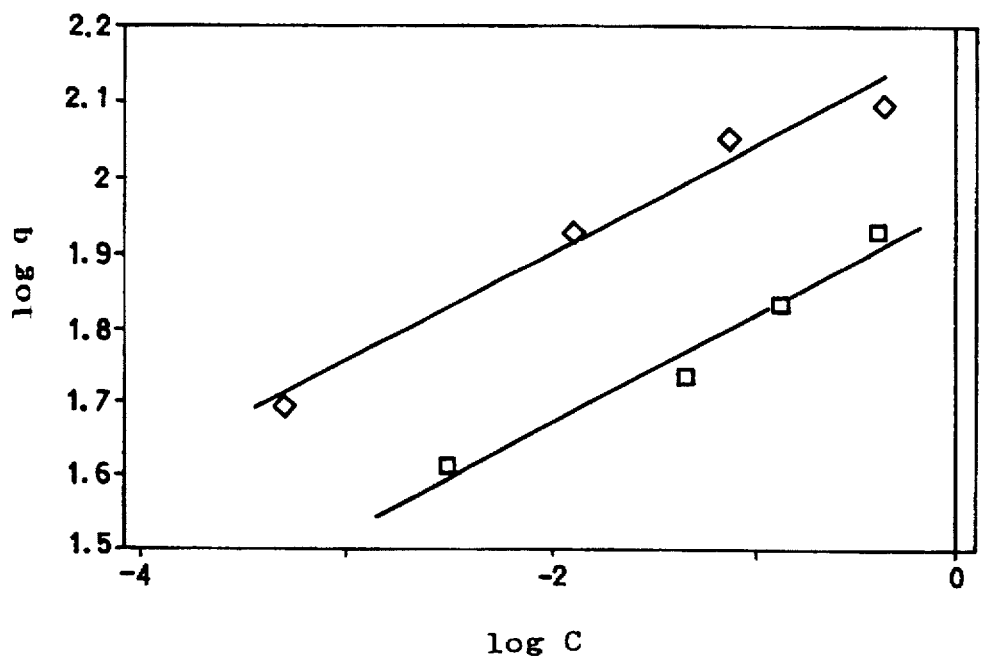
FIG. 3 is a graph showing a relation between an adsorption ratio of a motilin analogue adsorbed to microspheres in fat emulsions, each of which has a composition same with that referred to on FIG. 1 but is different in an amount of the electric charge adjusting agent, and concentration of the motilin analogue in aqueous phase of the fat emulsion.

Results are shown in FIG. 3. Freundlich's adsorption equilibrium as shown by following formula has been recognized on adsorption of the motilin analogue to microspheres in the fat emulsion. It has also been found that the adsorbed amount increases depending to the amount of electric charge adjusting agent.

logq=(a+b)logC q: concentration of adsorbent (mg/g)

C: concentration in aqueous phase a, b: constant

Example 5 and Test Example 6

Each of the fat emulsions (Prescriptions A and B used in Example 4) was mixed with an aqueous solution of [Leu$^{13}$]-motilin-Hse under conditions of ion intensity of 0.308 and pH 7 (final component concentrations: 0.1–1.0% fat emulsion, and 100 µg/ml motilin analogue) to check an amount of motilin analogue adsorbed to microspheres in the fat emulsion.

Each of the mixtures (pharmaceutical compositions) of the fat emulsion and aqueous solution of the motilin analogue was diluted by saline to check an amount of the motilin analogue adsorbed to microspheres in the fat emulsion.

Figure 4:
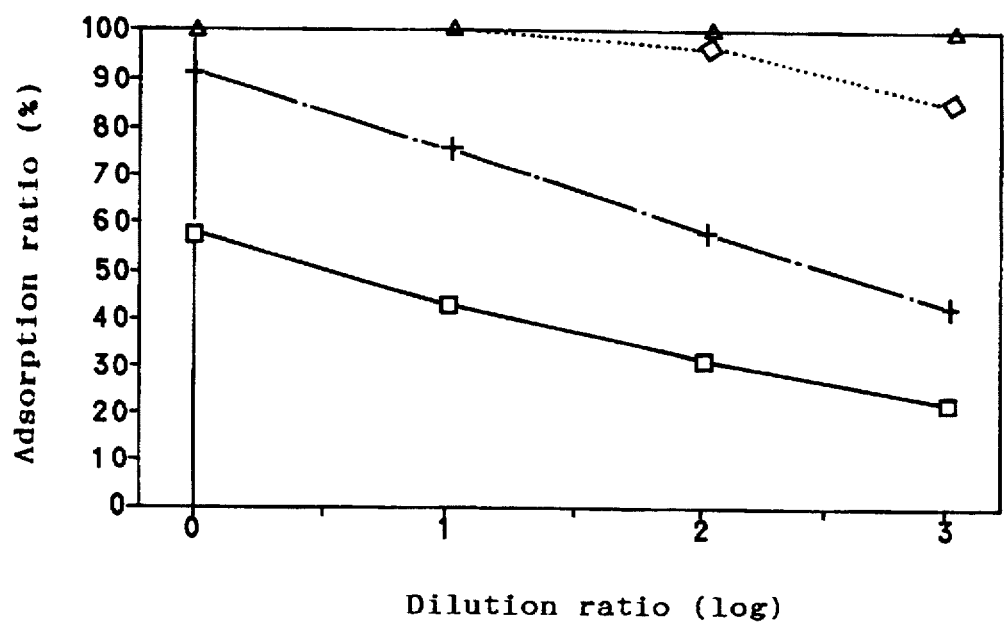
FIG. 4 is a graph showing a relation between an adsorption ratio of the motilin analogue adsorbed to microspheres in the fat emulsion which is one of those referred to on FIG. 3 and a dilution ratio of the fat emulsion.
Figure 5:
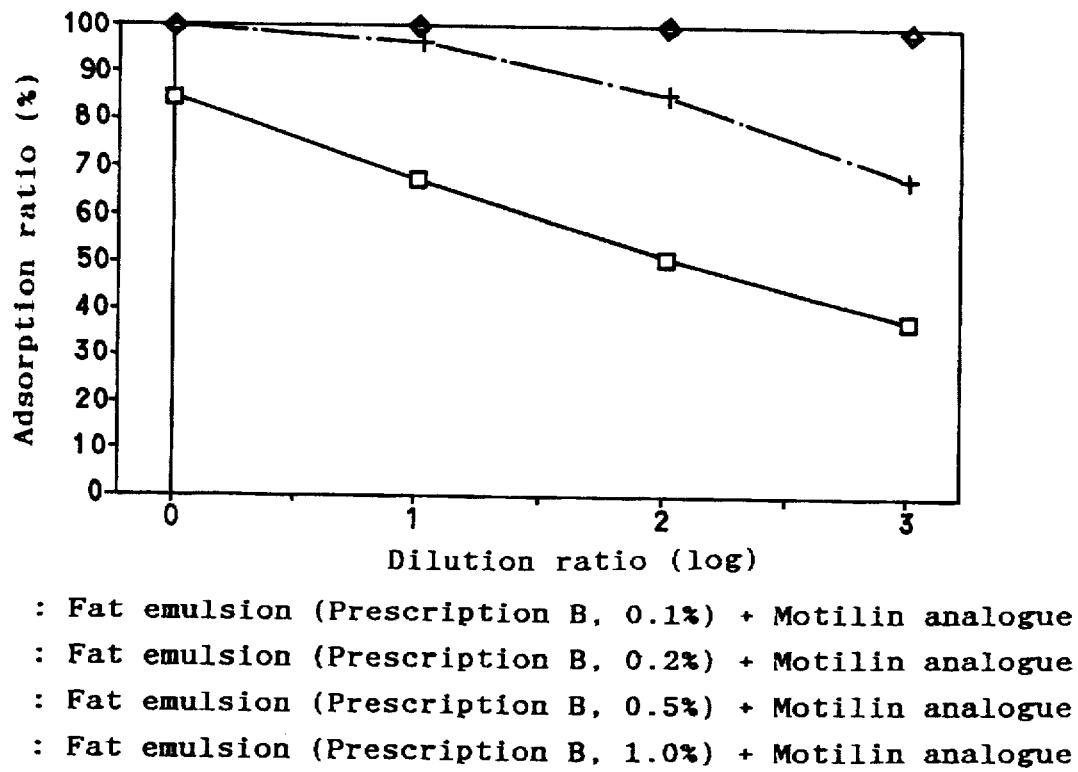
FIG. 5 is a graph showing a relation between an adsorption ratio of the motilin analogue adsorbed to microspheres in the fat emulsion which is the other of those referred to on FIG. 3 and a dilution ratio of the fat emulsion.
Figure 6:
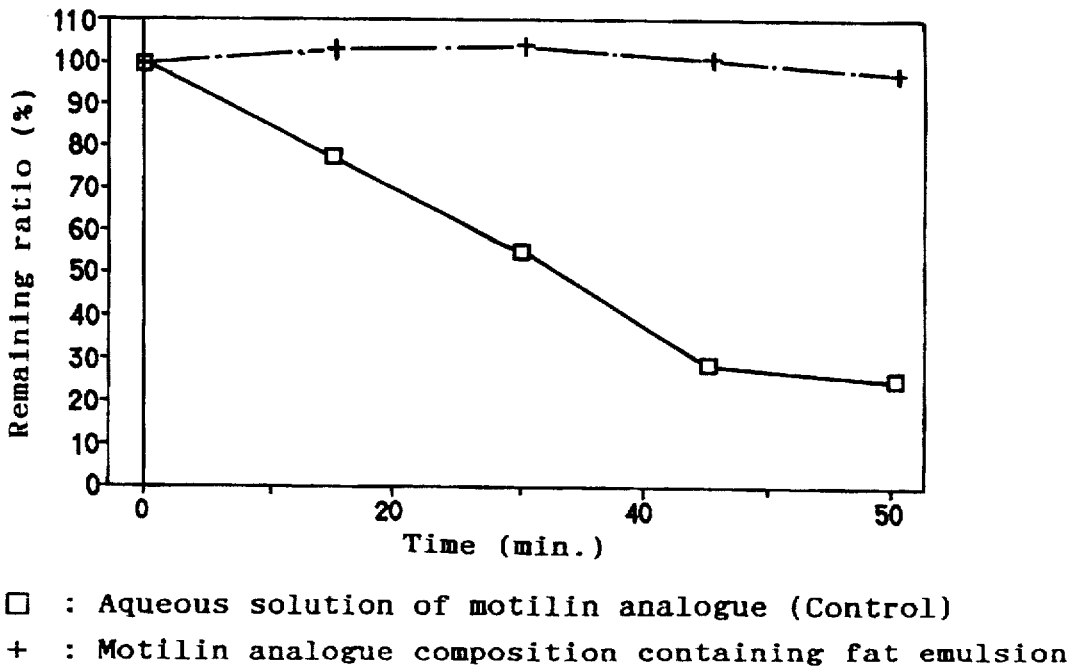
FIG. 6 is a graph showing results of measurements on remaining amount of a motilin analogue adsorbed to microspheres in an electric charge adjusted fat emulsion (composition according to the invention) and an aqueous solution of the motilin analogue (control), by acting thereto 1 μg/ml chymotrypsin and then occasionally carrying out the measurements.
Figure 7:
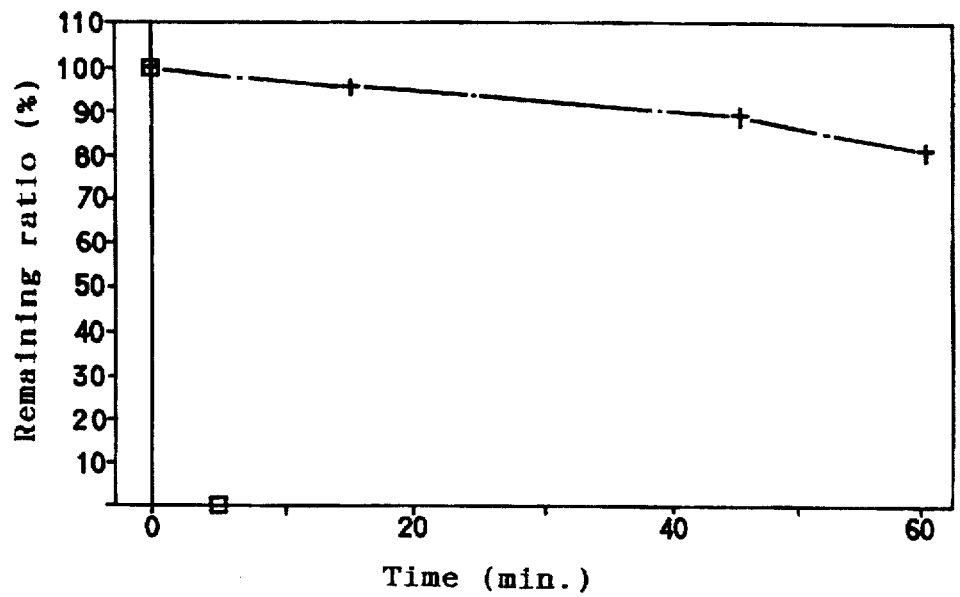
FIG. 7 is a graph similar to FIG. 6, in case of that concentration of the chymotrypsin was 250 μg/ml.
Figure 8:
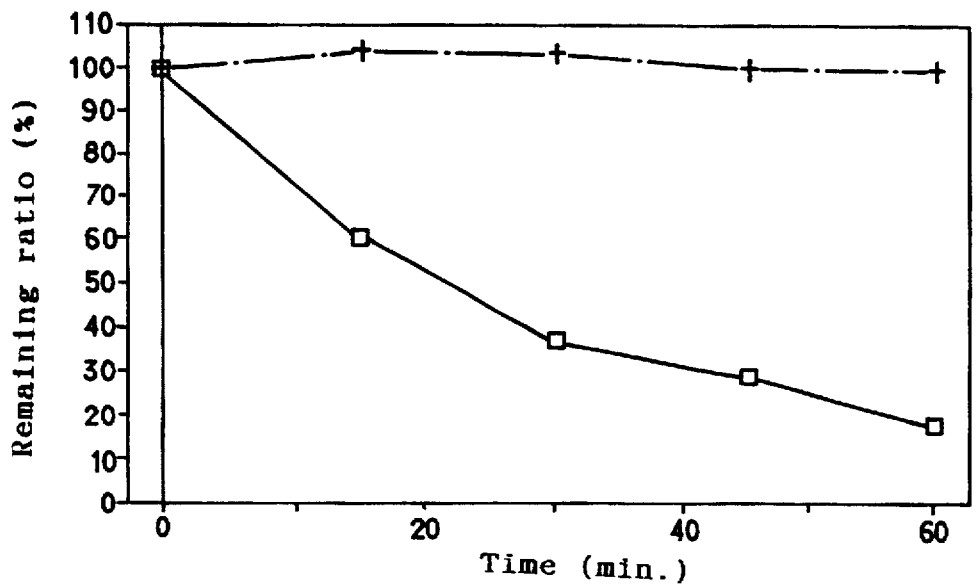
FIG. 8 is a graph similar to FIG. 6, in case of that trypsin of 0.38 μg/ml was acted.
Figure 9:
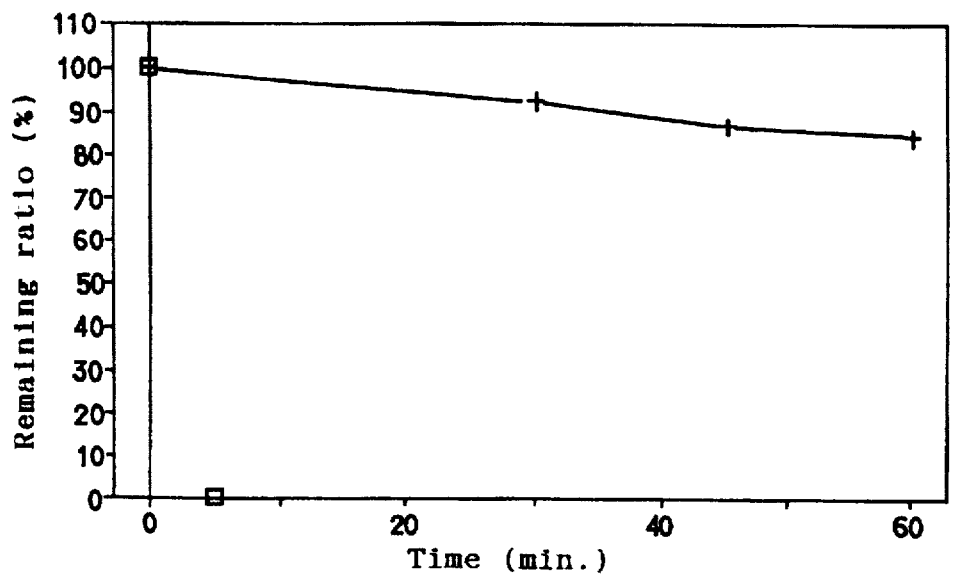
FIG. 9 is a graph similar to FIG. 8, in case of that the concentration of trypsin was 185 μg/ml.

Results are shown in FIGS. 4 and 5. As apparently seen therefrom, it has been found that an amount of the motilin analogue adsorbed to microspheres in the fat emulsion and an amount of same discharged from the microspheres can be controlled by an amount of the fat emulsion and an amount of the electric charge adjusting agent therein.

Example 6 and Test Example 7

(Evaluation on stability to enzyme)

A pharmaceutical composition was prepared by using the fat emulsion (Prescription B, prepared by Example 2) and an aqueous solution of [Leu$^{13}$]-motilin-Hse (pH 7.0, ion intensity of 0.01, final component concentrations: 2% fat emulsion, and 100 µg/ml motilin analogue).

α-Chymotrypsin solutions [2 µg/ml (0.106 IU/ml) and 500 µg/ml (26.4 IU/ml)] were prepared by dissolving α-chymotrypsin derived from bovine pancreas into phosphate buffer (pH 7.8). Trypsin solutions [0.46 µg/ml (6.8 IU/ml) and 370 µg/ml (3398 IU/ml)] were prepared by dissolving trypsin derived from bovine pancreas into phosphate buffer (pH 7.8).

Each of the pharmaceutical compositions was mixed with each of the enzyme solutions in equi-amount to incubate at 37° C. to occasionally and quantitatively measure an amount of the motilin analogue remaining therein.

An aqueous solution of the motilin analogue (100 µg/ml) containing no fat emulsion was also treated as above, as a control.

Results are shown in following Tables 4 and 5 as well as FIGS. 6–9. Under an assumption of that a decomposition reaction is proportioned to a concentration of enzyme, stability of the pharmaceutical composition becomes about 2,000 folds to chymotrypsin and about 5,000 folds to trypsin, in comparison with the aqueous solution of motilin analogue.

TABLE 4

(Decomposition of motilin analogue by chymotrypsin)

| Sample | Control | Pharmaceutical composition |
|---|---|---|
| Concentration of enzyme | 1 µg/ml | 250 µg/ml |
| Constant of decomposition velocity (min$^{-1}$) | $2.47 \times 10^{-2}$ (0.982)** | $3.05 \times 10^{-3}$ (0.982)** |
| Ratio of decomposition velocity | 1 | 1/2025 |

TABLE 5

(Decomposition of motilin analogue by trypsin)

| Sample | Control | Pharmaceutical composition |
|---|---|---|
| Concentration of enzyme | 0.38 µg/ml | 185 µg/ml |
| Constant of decomposition velocity (min$^{-1}$) | $2.73 \times 10^{-2}$ (0.995)** | $2.77 \times 10^{-3}$ (0.994)** |
| Ratio of decomposition velocity | 1 | 1/4925 |

In Tables 4 and 5,
**: correlation coefficient in formula of primary reaction.

Example 7 and Test Example 8
(Evaluation on Stability to Enzyme)

A stability to bronchial airway washing liquid (BAL solution) of guinea pig on a pharmaceutical composition as described in Example 3 and comprising [Leu$^{17}$]-VIP-Hse.hexylamide and fat emulsion was checked. Namely, Hartley male guinea pig (age of 6 weeks, body weight of about 300 g) was anesthetized with urethane to expose trachea and saline (4 ml) was gradually introduced into the airway and then recovered the same from the airway as BAL solution which was reserved at −80° C.

While, a fat emulsion (Prescription C) was prepared, which is substantially same with the Prescription B referred to in Example 4, excepting that hydrogenated soybean phosphatidylcholine and sodium dimyristoylphosphatidylglycerol were employed in amount of 0.4 g and 1.6 g, respectively.

By using each of the fat emulsions (Prescriptions B and C), sample B and C were prepared [Tris-HCl (pH 7.8), final composition concentrations: 0.4% fat emulsion, 200 µg/ml [Leu$^{17}$]-VIP-Hse.hexylamide, and 70% (V/V) BAL solution]. Each of the samples B and C was incubated at 37° C. to occasionary and quantitatively measure an amount of the VIP analogue remaining therein.

As a control, a solution containing no fat emulsion was also prepared and above procedure was carried out thereon.

Figure 10:
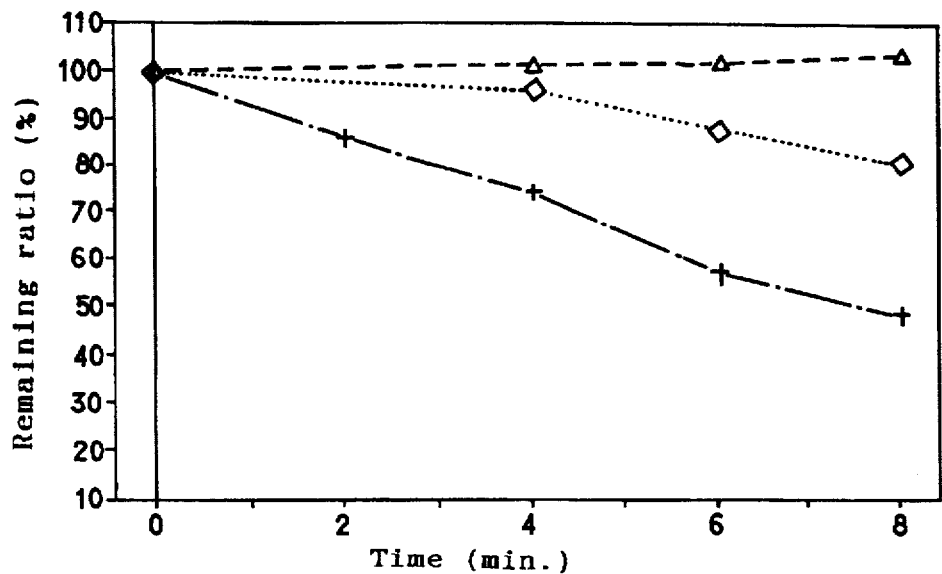
FIG. 10 is a graph showing results of measurements on remaining amount of VIP analogues adsorbed to microspheres in 2 electric charge adjusted fat emulsions (compositions according to the invention) and an aqueous solution of the VIP analogue (control), by acting thereto a solution of washed guinea pig bronchia and then occasionally carrying out the measurements.

Results are shown in following Table 6 and FIG. 10. As apparently seen therefrom, a half-value period of the composition containing the fat emulsion of Prescription B is extended about 3.5 folds in comparison with the control, while no decomposition was recognized on the composition containing the fat emulsion of Prescription C. These facts show that stability of the peptide to the enzyme can be remarkably increased by combining the same with the electric charge adjusted fat emulsion.

TABLE 6

| | Constant of decomposition | Half-value period of decomposition | |
|---|---|---|---|
| | velocity (hr) | hr | ratio |
| Control | 0.095 (0.994)** | 7.3 | 1.0 |
| Sample B | 0.027 (0.994)** | 25.2 | 3.5 |
| Sample C | No decomposition can be recognized | | |

In Table 6,
**: correlation coefficient in formula of primary reaction.

Example 8 and Test Example 9

A relaxant activity of VIP analogue to contraction of bronchia smooth muscle due to histamine was evaluated by Konzett-Roessler's method.

A fat emulsion of Prescription D was prepared, which was same with those of Prescription B and C referred to in Example 7, excepting that sodium dimyristoylphosphatidylglycerol (2.0 g) was employed and the hydrogenated soybean phosphatidylcholine was not used. Another fat emulsion of Prescription E was prepared, which is same with that of Prescription D, excepting that sodium dimyristoylphosphatidylglycerol was substituted with sodium dipalmitoylphosphatidylglycerol.

A composition (Samples B, C, D or E) was prepared by using the fat emulsion (Prescription B, C D or E) and [Leu$^{17}$]-VIP-Hse-hexylamide (Final component concentrations: 2% fat emulsion, and 100 µg/ml VIP analogue).

The relaxant activity of the compositions D and E as well as compositions B and C were evaluated as stated below by administrating the composition as 20 µg/kg based on the VIP analogue to experimental animals. An aqueous solution of the VIP analogue was also administrated, as control.

Experiment:

(A) Experimental animal; Hartley guinea pigs (male, age of 4 weeks).

(B) Anesthetic; Urethane (C) Artificial respiration; 40 strokes/min. (4–7ml/strokes).

(D) Inhibitor of Spontaneous respiration; Succinylcholine chloride (Suc), 1.2 mg/kg i.v.

(E) Contraction generator; Histamine (His), 5 µg/kg i.v.

(F) Operation procedure and measures;

A neck portion is incised under anesthesia to insert a cannula for a drug-line into a jugular vein, and another cannula for communicating to a transducer of the Konzett-Roessler's device is inserted into airway of the animal.

(G) Inhibition of adhesion to instruments; Pretreating instruments by 1% hardened castor oil.

(H) Administration schedule ;

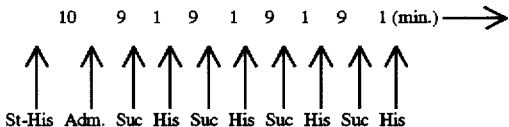

Adm.: Administration of the Test or Control Sample.

(I) Treatment of resulting data; Inhibition is calculated by following equation. Inhibition (%)=[1-(peak height due to His)/(peak height at St-His)]×100

Figure 11:
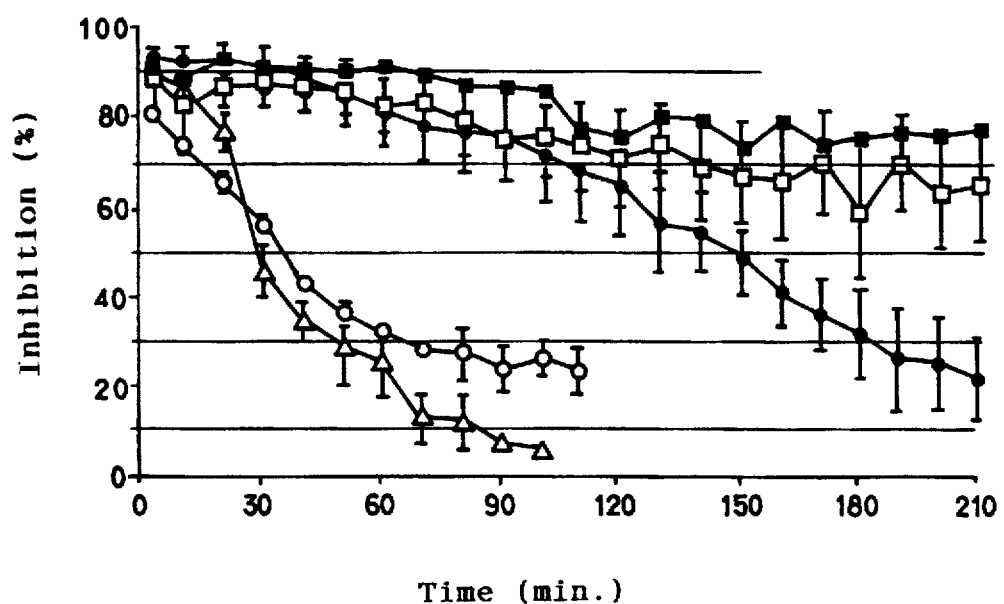
FIG. 11 is a graph showing results of measurements on relaxant activity of VIP analogue compositions (4 compositions according to the invention, as test samples and an aqueous VIP analogue solution, as control) to guinea pig airway smooth muscle contraction due to histamine.

(J) Results;

Results are shown in following Table 7 and FIG. 11. As apparently seen therefrom, acting period of time of the VIP analogue can remarkably be extended by making it into a composition with the fat emulsion, in comparison with the aqueous VIP analogue preparation.

TABLE 7

| Composition | Sample | | | | |
|---|---|---|---|---|---|
|  | B | C | D | E | Control |
| $ID_{50}$ | 34 | 151 | >210 | >210 | 29 |

In the Table, $ID_{50}$: period of time (min.) able to attaining 50% inhibition of bronchia smooth muscle contraction due of histamine.

Example 9 and Test Example 10

A test sample composition was prepared by mixing the fat emulsion of Prescription D prepared by Example 8 with eel calcitonin (4500 IU/mg, manufactured by Peninsula Laboratories, Inc.). Final component concentrations of the composition were 0.015% fat emulsion, and 0.03 μg eel calcitonin.

Control compositions were also prepared by dissolving eel calcitonin into 1% sodium acetate solution (pH 4.0) containing 0.1% bovine serum albumin (BSA). Final concentration of the eel calcitonin was 0.03 or 0.10 μg/ml.

To Wister male rats (age of 6 weeks, 3 animals in each of test and control groups) anesthetized by ethyl ether, the composition was rapidly injected from jugular vein and occasionally taken the blood to quantitatively measure an amount of calcium in its serum by using a measuring kit ("Calcium C Test-Wako" marketed from Wako Pure Chemicals Co., Ltd.) to prepare a graph showing relation between decreasing ratio in serum calcium and time lapsed to calculate an area under the curve, as an index of biological activity.

Figure 12:
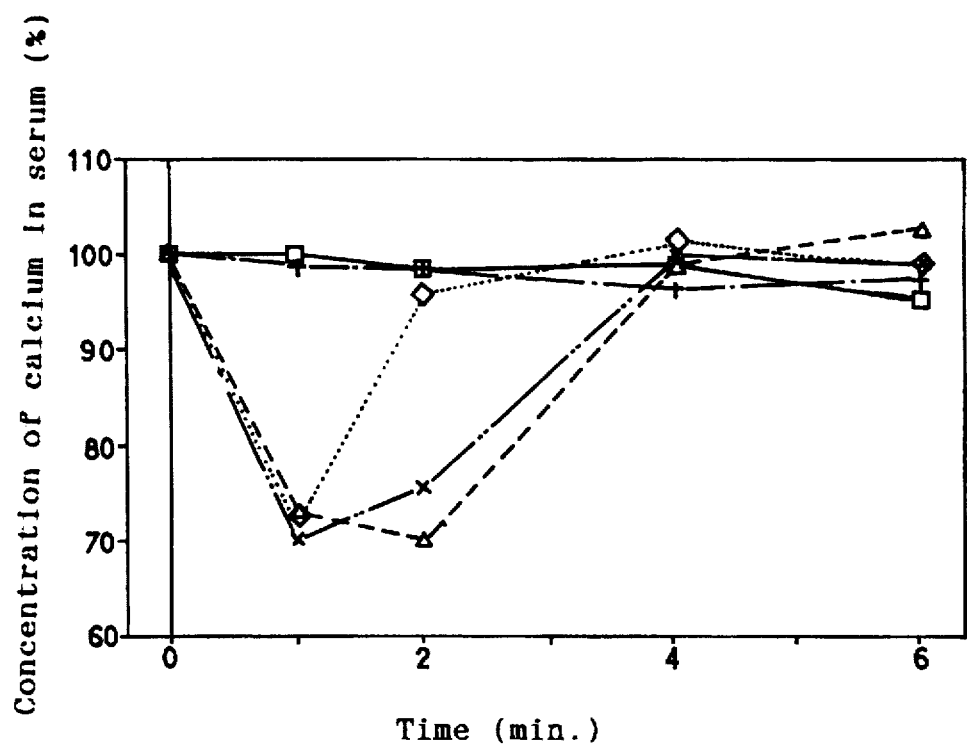
FIG. 12 is a graph showing results of measurements on an activity on decreasing of serum calcium concentration in rats due to eel calcitonin compositions (composition according to the invention, as test sample and aqueous eel calcitonin solution as controls).

Results are shown in following Table 8 and FIG. 12. As apparently seen therefrom, it has been found that the activity of the composition according to the invention is about 2 folds in comparison with the control composition and it is necessary to dose the control composition in about 3 folds in amount for providing substantially the same effect with the composition according to the invention.

TABLE 8

| Sample | Test | Control | |
|---|---|---|---|
| Amount (μg/ml/kg) | 0.03 | 0.03 | 0.10 |
| Activity (% . hr) | 70.9 ± 6.0 | 36.6 ± 7.4 | 74.0 ± 8.2 |

What is claimed is:

1. A pharmaceutical composition comprising a fat emulsion containing microspheres and having its electric charge adjusted to a negative value and a pharmaceutically active substance selected from the group consisting of a basic peptide and a basic protein, which pharmaceutically active substance is adsorbed to the microspheres in said fat emulsion.

2. The pharmaceutical composition as claimed in claim 1, wherein the composition contains at least one substance selected from the group consisting of an acidic phospholipid, a fatty acid, a bilic acid and a salt of such substances, as an agent for adjusting the electric charge of the fat emulsion.

3. The pharmaceutical composition as claimed in claim 1, wherein the pharmaceutically active substance is selected from the group consisting of [Leu$^{13}$]-motilin-Hse, [Leu$^{17}$]-VIP-Hse, [Leu$^{17}$]-VIP-Hse-hexylamide and calcitonin.

* * * * *

SEQUENCE LISTING ( 1 ) GENERAL INFORMATION:

( i i i ) NUMBER OF SEQUENCES: 2

( 2 ) INFORMATION FOR SEQ ID NO: 1 :

( i ) SEQUENCE CHARACTERISTICS:
        ( A ) LENGTH: 23 Amino acids
        ( B ) TYPE: Amino acid
        ( C ) STRANDEDNESS: Single
        ( D ) TOPOLOGY: Linear ( i i ) MOLECULE TYPE: Peptide ( i i i ) HYPOTHETICAL: No ( i v ) ANTI-SENSE: No ( i x ) FEATURE:
        ( D ) OTHER INFORMATION:
            Xaa ; Homoserine or homoserine-lactone ( x i ) SEQUENCE DESCRIPTION: SEQ ID NO : 1 :

Phe Val Pro Ile Phe Thr Tyr Gly Glu Leu Gln Arg Leu Gln Glu Lys Glu
             5                        10                    15

Arg Asn Lys Gly Gln Xaa
            20

( 2 ) INFORMATION FOR SEQ ID NO: 2 :

( i ) SEQUENCE CHARACTERISTICS:
        ( A ) LENGTH: 29 Amino acids
        ( B ) TYPE: Amino acid
        ( C ) STRANDEDNESS: Single
        ( D ) TOPOLOGY: Linear ( i i ) MOLECULE TYPE: Peptide ( i i i ) HYPOTHETICAL: No (iv) ANTI-SENSE: No (ix) FEATURE:
    (D) OTHER INFORMATION:
        Xaa ; Homoserine or homoserine-lactone, and
        C-terminus may be hexylamidized (xi) SEQUENCE DESCRIPTION: SEQ ID NO : 2 :

His Ser Asp Ala Val Phe Thr Gly Asn Tyr Thr Lys Leu Arg Lys Gln Leu
            5                   10                  15

Ala Ala Lys Lys Tyr Leu Asn Lys Ala Leu Lys Xaa
        20                  25